US005643599A

United States Patent [19]
Lee et al.

[11] Patent Number: 5,643,599
[45] Date of Patent: Jul. 1, 1997

[54] INTRACELLULAR DELIVERY OF MACROMOLECULES

[75] Inventors: Kyung-Dall Lee, Providence, R.I.; Daniel A. Portnoy, Philadelphia, Pa.; Joel A. Swanson, Brookline, Mass.

[73] Assignees: President and Fellows of Harvard College, Cambridge, Mass.; University of Pennsylvania, Philadelphia, Pa.

[21] Appl. No.: 486,764

[22] Filed: Jun. 7, 1995

[51] Int. Cl.$^6$ .................................................. A61K 9/127
[52] U.S. Cl. ........................................... 424/450; 436/829
[58] Field of Search ................................. 424/450, 184.1; 436/829

[56] References Cited

U.S. PATENT DOCUMENTS

| | | |
|---|---|---|
| 4,863,874 | 9/1989 | Wassef et al. ............................ 436/501 |
| 4,921,757 | 5/1990 | Wheatley et al. ...................... 428/402.2 |
| 4,925,661 | 5/1990 | Huang .................................... 424/85.91 |
| 5,225,212 | 7/1993 | Martin et al. ............................. 424/450 |

FOREIGN PATENT DOCUMENTS

| | | |
|---|---|---|
| 0256989A1 | 2/1988 | European Pat. Off. . |
| 0148551 | 7/1985 | WIPO . |
| WO93/25225 | 12/1993 | WIPO . |
| WO94/25616 | 11/1994 | WIPO . |
| 95/03788 | 2/1995 | WIPO . |
| 96/00792 | 1/1996 | WIPO . |

OTHER PUBLICATIONS

Lee, K-D, et al., "Delivery of Macromolecules into Cytosol Using Liposomes Containing Hemolysin from Listeria monocytogenes", J. Biol. Chem. 271 (13): 7249-7252 (1996).
Torchilin, V.P., et al., "pH-Sensitive Liposomes", J. Liposome Research 3 (2): 201-255 (1993).
Yamanaka, Chem Abstracts, 107, #29591.
Glushakova, Chem Abstracts, 103, #208093.
Glushakova, Chem Abstract, 103, 194758.
Yamanaka, H., et al., "Preparation of specific antiserum against *Vibrio vulnificus* hemolysin by immunization with hemolysin-bound liposomes", FEMS Microbiology Ltrs. 41:313-316 (1987).
Bron, R., et al., "Cellular Cytoplasmic Delivery of Polypeptide Toxin by Reconstituted Influenza Virus Envelopes (Virosomes)", Biochem, 33:9110-9117 (1994).
Bakker-Woudenberg, I. et al., Effect of Lipid Composition on Activity of Liposome-Entrapped Ampicillin against Intracelluar *Listeria monocytogenes*, Antimicrobial Agents and Chem., Oct. 1988, 1560-1564.
Choi, M. et al., pH-sensitive Liposomes Containing Polymerized Phosphatidylethanolamine and Fatty Acid, J. Biochem, 112, 694-699 (1992).
Chu, C. et al., Efficiency of Cytoplasmic Delivery by pH-sensitive Liposomes to Cells in Culture, Pharmaceutical Research, vol. 7, No. 8, 1990, 824-834.

Collins, D. et al., Structural and functional comparisons of pH-sensitive liposomes composed of phosphatidylethanolamine and three different diacylsuccinylglycerols, Biochimica et Biophysica Acta. 1025 (1990) 234-242 Elsevier.
Collins, D., Processing of exogenous liposome-encapsulated antigens in vivo generates class I MHC-restricted T cell responses. J. of Immunology, vol. 148, No. 11, 3336-3341, Jun. 1, 1992.
Connor. J. et al., pH-sensitive liposomes: Acid-induced liposome fusion, Proc. Natl. Acad. Sci. USA, vol. 81, 1715-1718, Mar. 1984.
Desiderio, J. and S.G. Campbell, Liposome-Encapsulated Cephalothin in the Treatment of Experimental Murine Salmonellosis, RES: J of Reticuloendothelial Soc. 34:279-287 (1983).
Desiderio, J. and S.G. Campbell, Immunization against experimental murine salmonellosis with liposome-associated O-antigen, Infection and Immunity, vol. 48, No. 3, Jun. 1985, pp. 658-663.
Düzgünes, N. et al., Proton-induced fusion of oleic acid-phophatidylethanolamine liposome, Biochemistry 24:3091-3098, 1985.
Fattal, E. et al., Liposome-entrapped ampicillin in the treatment of experimental murine listeriosis and salmonellosis, Antimicrobial Agents and Chemotherapy, vol. 35, No. 4, Apr. 1991, pp. 770-772.
Fidler, I. et al., Design of liposomes to improve delivery of macrophage-augmenting agents to alveolar macrophages Cancer Research 40:4460-4466 Dec. 1980.
Goren, M. et al., Prevention of phagosome-lysosome fusion in cultured macrophages by sulfatides of *mycobacterium tuberculosis*, Proc Natl. Acad. Sci USA, vol. 73, No. 7, Jul. 1976, pp. 2510-2514.
Harding, C. et al., Liposome-encapsulated antigens engender lysosomal processing for class II MCH presentation and cytosolic processing for class I presentation, J. of Immunology, 147:2860-63 (1991).
Harding, C. et al., Lipsome-encapsulated antigens are processed in lysosomes, recycled, and presented to T cells, Cell 64:393-401, Jan. 25, 1991.
Hart. P.D'arcy and M. Young, The effect of inhibitors and enhancers of phagosome-lysosome fusion in cultured macrophages on the phagosome membrances of ingested yeasts, Exp. Cell Res. 118 (1979) 365-375.
Harwood, J., Understanding liposomal properties to aid their clinical usage, TIBS 17, Jun. 1992, 203-204.
Hazemoto, N. et al., pH-sensitive liposomes composed of phosphatidylethanolamine and fatty acid, Chem. Pharm. Bull. 38(3) 748-751 (1990).

(List continued on next page.)

*Primary Examiner*—Gollamudi S. Kishore, PhD
*Attorney, Agent, or Firm*—Wolf, Greenfield & Sacks, P.C.

[57] ABSTRACT

An improved liposome and related methods for using the liposome to facilitate the delivery of an extracellular agent to the cytoplasm of a target cell are provided. The improved liposomes include a phagosomal membrane permeabilizer, such as a hemolysin.

38 Claims, No Drawings

OTHER PUBLICATIONS

Nair, S. et al., Soluble proteins delivered to dendritic cells via pH-sensitive liposomes induce primary cytoxic T lymphocyte response in vitro, J. Exp. Med., 175:609–612, Feb. 1992.

Paphadjopoulos, D., et al., Sterically stabilized liposomes: improvements in pharmacokinetics and antitumor therapeutic efficacy, Proc. Natl Acad. Sci. USA 88:11460–11464, Dec. 1991.

Reddy, R. et al., pH sensitive liposomes provide an efficient means of sensitizing target cells to class I restricted CTL recognition of a soluble protein, J. of Immunol. Methods 141:157–163 (1991).

Straubinger, R., [28] pH-sensitive liposomes for delivery of macromolecules into cytoplasm of cultured cells, Methods of Enzymology 221:361–376 (1993).

Straubinger, R. et al., Endocytosis of liposomes and intracellular fate of encapsulated molecules: encounter with a low pH compartment after internalization in coated vesicles, Cell 32:1069–1079, 1983.

Tadakuma, T. et al., Treatment of experimental salmonellosis in mice with streptomycin entrapped in liposomes, Antimicrobial Agents and Chemotherapy, vol. 28, No. 1, Jul. 1985, pp. 28–32.

INTRACELLULAR DELIVERY OF MACROMOLECULES

GOVERNMENT SUPPORT

The invention described herein was supported in part by a grant from the National Institutes of Health. The government has certain rights in this invention.

FIELD OF THE INVENTION

This invention relates to methods and compositions containing an improved liposome for facilitating the delivery of an extracellular agent into the cytoplasm of a target cell. More particularly, the invention relates to improved liposomes which reduce the likelihood of lysosomal degradation of the agent following its delivery to the target cell and the use of the improved liposomes in pharmaceutical, diagnostic and genetic engineering applications.

BACKGROUND OF THE INVENTION

Liposomes are vesicles with an aqueous interior enclosed by one or more phospholipid bilayers. Such vesicles have demonstrated utility as vehicles for delivering therapeutic and/or diagnostic agents to target tissues or organs. Liposomes that have been introduced into the circulatory system are removed therefrom by macrophages, particularly those of the spleen and liver that are in direct contact with the circulatory system, in a process referred to as phagocytosis. Phagocytosis is essential for immune surveillance and response. Although nearly all microorganisms phagocytosed by macrophages are degraded enzymatically following fusion of the phagosomes (containing the microorganisms) with host lysosomes, some pathogens survive phagocytosis by interrupting the natural progression of the phagosome to the host lysosomes. Indeed, some of the most significant pathogens, e.g., the agents of typhoid fever, Legionnaire's disease and tuberculosis, evade macrophage defenses by taking up residence within the phagosomes of macrophages.

Several antibiotics have been encapsulated into liposomes for the purpose of treating intracellular parasites in macrophages. For example, amphotericin B, encapsulated inside liposomes, reportedly has been used to treat leishmaniasis, histoplasmosis and candidasis, (Alving, C. et al., *Proc. Natl. Acad. Sci. USA* 75:2959–2963 (1978); Szoka, F. et al., *Antimicrobial Agents and Chemotherapy* 31:421–429 (1987)). Liposomes containing amikacin reportedly exhibit improved efficacy in the treatment of *Mycobacterium avium* complex, a significant pathogen of AIDS patients (Düzgünes, N. et al., *Antimicrobial Agents and Chemotherapy* 32:1404–1411 (1988)). Liposomes containing gentamicin or ampicillin reportedly are slightly more effective than free drug when tested in a mouse model of Salmonellosis (Fattal, E. et al., *Antimicrobial Agents and Chemotherapy* 35:770–772 (1991); Swenson, C. et al., *Antimicrobial Agents and Chemotherapy* 34:235–240 (1990)).

Despite these reported successes, one problem inherent to conventional liposome-based drug delivery is that conventional liposomes cannot deliver drugs or other agents to the cytoplasm of the target cell. This is because once the liposome has been internalized within a phagosome of the target cell, the phagosomal membrane acts as a barrier and blocks passage of the liposome-entrapped drug or agent to the cytoplasm. Accordingly, there currently is no effective method to deliver a membrane impermeant drug to the cytoplasm of a cell to enable the drug to interact with its intended target.

Moreover, conventional liposome-delivered agents often are degraded before reaching their intracellular target because liposomes ingested by macrophage phagocytosis are delivered into lysosomes in the same manner as phagocytosed particles or microorganisms. In addition, not every liposome-encapsulated drug that is phagocytosed by a pathogen-infected macrophage will be delivered to every phagosome that contains a pathogenic microorganism, i.e., some pathogens will avoid exposure to the drug simply because the liposome is not delivered to the phagosome in which the pathogen resides. The intracellular pathogen or other target of drug therapy may avoid the drug because it resides within the cell but outside the phagosome.

In view of the foregoing, there is still a need for improved liposomes for facilitating the delivery of extracellular agents, such as antibiotics, into target cells to deliver the extracellular agent to an intracellular (cytoplasmic) target. Such improved liposomes would deliver the extracellular agent to the intracellular target structure with reduced lysosomal enzyme catalyzed agent degradation in comparison with the degradation observed in connection with drug delivery using the prior art liposomes. In addition, the improved liposomes would permit the delivery of a higher effective intracellular concentration of the extracellular agent to the intracellular target and would permit the targeting of extracellular agents to particular structures within the cytoplasm of the target cell.

SUMMARY OF THE INVENTION

The present invention overcomes the problems of the prior art by providing an improved liposome for delivering a membrane impermeant, extracellular agent to the cytoplasm of a target cell. Unlike the liposomes of the prior art, the liposomes of the present invention are designed and constructed to reduce lysosomal degradation of the liposome-entrapped agent within the target cell. In particular, the improved liposomes include an agent delivery enhancer which facilitates transport of the extracellular agents from the phagocytosed liposomes to the target cell cytoplasm, thereby reducing lysosomal degradation of the liposome-delivered extracellular agents within the phagosome following fusion of the phagosome to a lysosome. As a result, the invention advantageously offers compositions and methods for delivering to virtually any type of cell that is capable of internalizing a liposome, higher effective concentrations of extracellular agents in the cytoplasm of target cells than previously could be achieved.

The compositions and methods of the invention are based upon the recognition that an improved liposome for delivering an extracellular agent to a target cell should satisfy several criteria. First, the liposome should be efficiently internalized by the target cell. Second, the liposome should release its contents (the "liposome-entrapped agent") into the phagosome at some time before or after fusion of the phagosome with the lysosome. Preferably, the liposome releases its contents before fusion with the lysosome. Third, the liposome should contain an agent delivery enhancer that is capable of permeabilizing the phagosomal membrane to an extent that is sufficient to permit the liposome-entrapped agent to diffuse into the target cell cytoplasm. The improved liposomes can be used to deliver, for example, (i) antimicrobial drugs into macrophages for treating cytoplasmic microbial infections, (ii) proteins/peptides into antigen presenting cells for presentation via class I major histocompatibility complex molecules and (iii) nucleic acids into target cells for gene expression and regulation of gene transcription and translation.

According to one aspect of the invention, a liposome composition for delivering a membrane impermeant, extracellular agent to the cytoplasm of a target cell is provided. The liposomes are made of vesicle-forming phospholipids using, for example, conventional dispersion methods. In the particularly preferred embodiments, the liposomes are pH-sensitive liposomes, e.g., the liposomes are stable at neutral pH but are unstable (and release their contents) at acidic pH (e.g., pH 5 to pH 6). Protocols for forming and using pH-sensitive liposomes are known to those of ordinary skill in the art. See, e.g., Chu, C.-J., et al., *Pharmaceut. Res.* 7:824–834 (1990). In general, liposomes formed of oleic acid plus phosphatidylethanolamine or cholesterylhemisuccinate plus phosphatidylethanolamine are stable at neutral pH but are unstable at acidic pHs.

The liposomes include at least one agent delivery enhancer that is a phagosomal membrane permeabilizer and may contain other agent delivery enhancers, e.g., lysosomal fusion inhibitors, which influence movement of the extracellular agent from the liposome to other structures in the target cell. A lysosome fusion-inhibitor refers to a compound which inhibits fusion between a phagosome and a lysosome. Such compounds are known to those of ordinary skill in the art and can be identified using no more than routine experimentation using the procedures disclosed herein. The sulfatides, a closely related class of glycolipids, and the lectins are exemplary lysosome fusion inhibitors. See, e.g., Goren, et al. *P.N.A.S. U.S.A.* 73:2510–2514 (1976) and Hart, P. D. and M. R. Young, *Exp. Cell Res.* 118:365–375 (1979) for a discussion of the proposed mechanism by which sulfatides are believed to inhibit phagosome/lysosome fusion in a mouse model system.

A phagosomal membrane permeabilizer refers to a compound which, from within the phagosome, creates pores in the phagosome membrane that are sufficient in size to allow the passage of agents from within the phagosome to the cytoplasm. As used herein, "phagosome" is not limited to the endocytic compartment of a macrophage but refers instead to any endocytic compartment of any cell that is capable of internalizing a liposome. Although membrane permeabilizers are known to those of ordinary skill in the art and additional membrane permeabilizers can be identified using no more than routine experimentation, the delivery and use of membrane permeabilizers to phagosomes for the purpose of permeabilizing phagosomal membranes has not previously been reported.

Exemplary membrane permeabilizers which can be used as phagosomal membrane permeabilizers include the hemolysins, e.g., lysteriolysin O, streptolysin O and perfringolysin O. See, e.g., Portnoy, D. A., et al. *Infection and Immunity* 60:2710–2717 (1992) for a discussion of the hemolysins and in particular, for a discussion of the pore-forming properties of these molecules. The preferred phagosomal membrane permeabilizer is listeriolysin O (LLO) from *Listeria monocytogenes*. In a particularly preferred embodiment, the improved liposome contains a phagosomal membrane permeabilizer (e.g., listeriolysin O) and further includes a lysosome fusion-inhibitor (e.g., a sulfatide or lectin).

Alternative phagosomal membrane permeabilizers are identified in screening assays which detect the ability of a putative phagosomal membrane permeabilizer to confer upon a liposome the ability to deliver a liposome-entrapped extracellular agent to the target cell cytoplasm. Alternative lysosome fusion-inhibitors are identified in screening assays which detect the ability of the putative lysosome fusion-inhibitor to confer upon a liposome the ability to deliver the liposome-entrapped extracellular agent to the target cell with delayed fusion of the phagocytosed liposome to the target cell lysosome. Such screening assays rely upon physical measurements or functional activity assays to determine whether transport of the extracellular agent from the phagosome to the cytoplasm has occurred. Exemplary screening assays are described in the Examples. In the particularly preferred screening assays, the extracellular agent is a fluorescent molecule or other easily detectable molecule. An extracellular agent that is a fluorescent molecule is particularly useful because it permits simultaneous detection of phagosome/lysosome fusion and/or transphagosomal membrane transport of the extracellular agent into the target cell cytoplasm.

The present invention provides methods and liposomal compositions for delivering an extracellular agent across the membrane of a target cell and into the target cell cytoplasm. Although the preferred target cells are macrophages, the liposomes of the invention can be used to deliver the extracellular agent to virtually any cell that is capable of liposome uptake including, for example, monocytes, B cells, T cells, fibroblasts, neutrophils, endothelial cells and tumor cells. Accordingly, methods for making a pharmaceutical composition containing the claimed liposomal composition and methods for using the claimed liposomal composition in vitro and/or in vivo to deliver the liposome-entrapped extracellular agent to a variety of cell types also are provided.

The extracellular agent has an intracellular activity, such as an antibiotic activity, an antigenic determinant activity, a nucleic acid hybridizing activity or a gene expression activity. The invention is particularly useful for delivering membrane impermeant, extracellular agents to the cytoplasm of a target cell. As used herein, a membrane impermeant, extracellular agent refers to an extracellular agent which cannot penetrate the target cell at a sufficient concentration to modulate its intracellular activity. Exemplary extracellular agents that can be delivered in accordance with the methods of the invention include peptides, proteins, oligonucleotides, nucleic acids, antibiotics, antimicotics, antiviral agents, anti-cancer agents, enzymes, enzyme modulators, and imaging agents. In the particularly preferred embodiments, the exogenous agent is a peptide, a protein (e.g., containing an antigenic determinant for immune system modulation), an oligonucleotide (e.g., an antisense oligonucleotide), a nucleic acid (e.g., a gene under the control of a promoter) or an antibiotic (e.g., gentamycin, amphotericin B, amikacin, ampicillin). In a particularly preferred embodiment, the extracellular agent is an antibiotic that is useful for treating a disease attributable to an intracellular microorganism such as typhoid fever, Legionnaire's disease, tuberculosis, leishmaniasis, histoplasmosis, candidiasis, Mycobacterium avium complex and Salmonellosis.

According to yet other aspects of the invention, pharmaceutical compositions and methods for making the pharmaceutical compositions are provided. The methods involve preparing the improved liposomes of the invention and placing these compositions in pharmaceutically acceptable carriers. Such carriers are well known to those of ordinary skill in the art of liposome drug delivery.

According to still another aspect of the invention, a method for facilitating the intracellular release of a liposome-entrapped extracellular agent is provided. The method involves entrapping a selected extracellular agent within an improved liposome of the invention to form a liposome-entrapped extracellular agent and contacting the target cell with the liposome-entrapped extracellular agent for a time sufficient to permit internalization of the liposome-entrapped extracellular agent by the target cell.

According to yet another aspect of the invention, a method for facilitating the release of phagosomal-entrapped agents from phagosomes contained in a target cell are provided. The method involves contacting the target cell with a liposome of the invention for a time sufficient to permit phagocytosis of the liposome by the target cell.

These and other aspects of the invention as well as various advantages and utilities will be more apparent with reference to the detailed description of the preferred embodiments. All patents, patent publications and references identified in this document are incorporated in their entirety herein by reference.

DETAILED DESCRIPTION OF THE INVENTION

The instant invention embraces methods and compositions for delivering an extracellular agent having an intracellular activity across the membrane of a target cell to an intracellular location. More particularly, the methods and compositions of the invention are directed to an improved liposome composition that is designed and constructed to deliver a membrane impermeant, extracellular agent to the target cell cytoplasm. The improved liposomes include a phagosomal membrane permeabilizer (e.g., a hemolysin such as listeriolysin O, "LLO") which facilitates the transport of the liposome-entrapped agent across the phagosomal membrane and into the target cell cytoplasm.

According to one aspect of the invention, an improved liposome is provided. The improved liposome includes vesicle-forming lipids and at least one agent delivery enhancer that is a phagosomal membrane permeabilizer contained within the liposome. The phrase, "vesicle-forming lipids" is readily understood by those of ordinary skill in the art to mean lipids that are capable of forming liposome vesicles. See, e.g., U.S. Pat. No. 5,225,212, issued to Martin et al. Exemplary vesicle-forming lipids include phosphatidyl-choline (PC), phosphatidylserine (PS), phosphatidylinositol (PI), cholesterylhemisuccinate (CHEMS), phosphatidylethanolamine (PE), oleic acid (OA), phosphatidic acid (PA), phosphatidylglycerol (PG), monosialoganglioside (GM1), phosphatidylethanolamine coupled to polyethylene glycol (PEG-PE, available from Avanti Polar Lipids, Birmingham, Ala.) and cholesterol.

Typically, the liposomes contain (i) phosphatidylcholine in an amount ranging from about 50% to about 100% of the total vesicle-forming lipid; (ii) at least one of phosphatidylserine, phosphatidylglycerol, phosphatidic acid, and phosphatidylinositol in an amount ranging from about 0% to about 100% of the total vesicle-forming lipid; (iii) GM1 and/or PEG-PE in an amount ranging from about 0% to about 30% of the total vesicle-forming lipid; and (iv) cholesterol in an amount ranging from about 0% to about 50% of the vesicle-forming lipid. More preferably, the liposomes contain (i) phosphatidylcholine in an amount ranging from about 50% to about 100% of the vesicle-forming lipid; (ii) at least one of phosphatidylserine, phosphatidylglycerol, phosphatidic acid, and phosphatidylinositol in an amount ranging from about 0% to about 35% of the vesicle-forming lipid; (iii) GM1 and/or PEG-PE in an amount ranging from about 0% to about 10% of the vesicle-forming lipid; and (iv) cholesterol in an amount ranging from about 0% to about 50% of the vesicle-forming lipid. Most preferably, the liposomes contain (i) phosphatidylcholine in an amount ranging from about 50% to about 100% of the vesicle-forming lipid; and (ii) at least one of phosphatidylserine, phosphatidylglycerol, phosphatidic acid, phosphatidylinositol, GM1 and PEG-PE in an amount ranging from about 0% to about 10% of the vesicle-forming lipid.

The liposomes disclosed herein can be constructed to be pH-sensitive by including a pH-sensitive lipid in the liposome formulation. A pH sensitive liposome refers to a liposome which is designed and constructed so that the liposome structure decomposes (e.g., due to destabilization of the bilayer) when the liposome is exposed to a pH that differs from the pH at which the liposome was constructed. In general, pH sensitive liposomes include the above-identified vesicle-forming lipids plus at least one pH-sensitive lipid. As used herein, a pH-sensitive lipid refers to a lipid which contains a polar end (that is negatively charged at neutral pH) and a non-polar end. The polar end of the pH-sensitive lipid is protonated at pH 6.5 or lower. Accordingly, at mildly acidic pHs, protonation of the polar end of the pH-sensitive lipid destabilizes the polar bilayer and thus, destabilizes the liposome. pH-sensitive lipids include molecules which are naturally occurring (e.g., oleic acid) or synthetic (e.g., diacyl-glycerol-3-succinate, Avanti Polar Lipids, Birmingham, Ala.).

The particularly preferred liposomes are pH sensitive liposomes which contain one or more of the above-identified (non-pH sensitive) vesicle-forming lipids plus the pH-sensitive lipids phosphatidylethanolamine together with CHEMS and/or phosphatidylethanolamine together with oleic acid. It is the pH-sensitive properties of these pH-sensitive lipids which confer pH-sensitivity on the liposome. In a particularly preferred embodiment, the liposome is a pH sensitive liposome containing phosphatidylethanolamine and/or phosphatidylcholine in an amount ranging from about 50% to about 100% of the total vesicle-forming lipid, CHEMS and/or oleic acid in an amount ranging from about 0% to about 50% of the total vesicle-forming lipid, and at least one of phosphatidylserine, phosphatidylglycerol, phosphatidic acid, phosphatidylinositol, GM1 and PEG-PE in an amount ranging from about 0% to about 10% of the total vesicle-forming lipid. Exemplary pH-sensitive lipids and/or liposomes are described in U.S. Pat. No. 4,925,661, issued to Huang; Collins, D. C., et al., Biochem. Biophys. Acta 1025:234–242 (1990); Lai, et al., Biochem. 24:1654–1661 (1985); Connor, J. And L. Huang, J. Cell Biol. 101:582–589 (1985); and Chu, et al., Pharmaceut. Res. 7:824–834 (1990).

The liposomes of the invention contain at least one agent delivery enhancer that is a phagosomal membrane permeabilizer. As used herein, an "agent delivery enhancer" refers to a compound that confers upon the liposome, the ability to deliver a liposome-entrapped extracellular agent to the cytoplasm of a target cell. An agent delivery enhancer that is a phagosomal membrane permeabilizer is a compound which renders the target cell phagosome membrane permeable to agents contained therein, thereby reducing lysosomal degradation of phagosome-entrapped agents by allowing the entrapped agents to escape from the phagosome before or after fusion with the lysosome.

Phagosomal membrane permeabilizers are believed to interrupt the normal course of lysosomal enzyme catalyzed degradation of the liposome-entrapped extracellular agent following delivery of the liposome to the target cell phagosome and fusion of the phagosome with the target cell lysosome. Following delivery to the phagosome, acidic pH-sensitive liposomes typically breakdown (decompose) fairly rapidly because of the slightly acidic pH of the phagosome interior (between about pH 5.0 and about pH 6.). Liposomes that are not pH-sensitive also decompose within the phagosome but at a slower rate than the decomposition rate that is believed to occur for the above-described pH-sensitive liposomes. By combining pH sensitivity with phagosomal membrane permeability, the particularly preferred pH sensitive liposomes of the invention represent an improvement over conventional pH sensitive liposomes. Because LLO exhibits enhanced pore-forming activity at typical phagosome pH values (pH 5.0–6.0), LLO is a particularly preferred membrane permeabilizing agent (Portnoy, et al., *Infect. Immun.* 60:2710–2717 (1992)). It is generally believed that most hemolysins act at the plasma membrane.

Although not intending to be bound by any particular theory or mechanism, it is believed that the phagosomal membrane permeabilizers form pores or channels in the phagosome membrane, thereby allowing the agents entrapped therein to leak out of the phagosome and into an intracellular location (e.g., the cytoplasm). The pores that are made by the hemolysins allow diffusion in both directions across the membrane. By facilitating transport of the extracellular agent out of the phagosome before the phagosome fuses with the lysosome and/or before the lysosomal enzymes have degraded a significant amount of the extracellular agent, the phagosomal membrane permeabilizers reduce the extent of lysosomal degradation of the extracellular agent relative to that which is observed using conventional liposomes.

In a particularly preferred embodiment, the improved liposomes contain between about five and about one-hundred molecules of the phagosomal membrane permeabilizer per liposome. Exemplary phagosomal membrane permeabilizers include the hemolysins the phospholipases (see, e.g., Camilli, A., et al., *J. Exp. Med.* 173:751–754 (1991)), and a pore-forming toxins (e.g., an alpha-toxin). In general, any agent that is capable of permeabilizing a membrane can be used as a phagosomal membrane permeabilizer, provided that it can be incorporated into a liposome in accordance with the methods disclosed herein.

The hemolysins are the preferred class of phagosomal membrane permeabilizers. In a particularly preferred embodiment, the phagosomal membrane permeabilizer is the listeriolysin O from *Listeria monocytogenes*. The hemolysins are soluble proteins that are expressed by diverse species of gram-positive bacteria. Exemplary hemolysins include lysteriolysin O (LLO), streptolysin O (SLO) and perfringolysin O (PFO). It is generally believed that the hemolysins bind to membranes and form pores by self-assembling into polymeric structures. Listeriolysin O is a preferred phagosomal membrane permeabilizer because listeriolysin O advantageously exhibits greater pore-forming ability at mildly acidic pH (the pH conditions within the phagosome), thereby facilitating delivery of the liposome contents to the cytoplasm (see, e.g., Portnoy, et al., *Infect. Immun.* 60:2710–2717 (1992)). Because the sequence of LLO is known (see, Mengaud, J., et al., *Infect. Immun.* 56:766–772 (1988)), routine genetic engineering procedures such as, for example, site directed mutagenesis or gene truncation, can be used to create mutants having improved hemolytic activity. For example, mutant hemolysins can be constructed in which the highly conserved cysteine residues of the hemolysins (e.g., cysteine 460 in PFO and cysteine 486 in LLO) are replaced by conservative amino acid substitutions which are not subject to reduction in order to prepare oxidation/reduction-insensitive hemolysin mutants which exhibit improved hemolytic activity.

Alternatively, mutant LLOs can be selected from naturally occurring mutants by, for example, identifying bacteria which contain LLOs that are capable of lysing cells over a narrow pH range, preferably the pH range which occurs in phagosomes (pH 5.0–6.0), or under other conditions (e.g., ionic strength) which occur in the phagosomes.

Yet other improved hemolysins include, for example, LLO that has been genetically engineered to include the amino acid sequences of extracellular agents that are peptides or proteins and that are intended to be delivered to the target cell cytoplasm (e.g., by forming a nucleic acid construct which encodes LLO and the peptide/protein in the same reading frame and expressing the novel "fusion protein" in accordance with standard procedures). In this manner, peptides and proteins intended for delivery to class I major histocompatibility complex molecules for antigen presentation can be delivered to the target cell cytoplasm.

As noted above, the phrase "phagosomal membrane permeabilizer" refers to a compound that is capable of rendering a phagosomal membrane permeable to agents contained in the phagosome. Screening assays for identifying putative phagosomal membrane permeabilizers which form pores in the phagosome or otherwise render the phagosomal membrane permeable to agents contained therein (e.g., extracellular agents originating from a liposome or other phagosome-entrapped agents, such as phagosome-entrapped pathogens) are described in the Examples. In general, the screening assays measure the ability of a putative phagosomal membrane permeabilizer to confer on a liposome the ability to render a target cell phagosome permeable to a labeled agent (e.g., fluorescent agent, radiolabeled agent) that is contained in the phagosome.

The preferred phagosomal membrane permeabilizers have amino acid sequences that are identical to the amino acid sequences of the naturally-occurring hemolysins. The amino acid sequence of LLO, as well as the sequence homology between this and other members of the hemolysin class of molecules, have been published. See, e.g., Mengaud, J., et al., Infect. Immun. 56:766–772 (1988) and Portnoy, et al., Infect. Immun. 60:2710–2717 (1992)). In a particularly preferred embodiment, the phagosomal membrane permeabilizer has an amino acid sequence that is identical to the amino acid sequence of listeriolysin O from *Listeria monocytogenes*.

Optionally, the liposomes contain a second category of agent delivery enhancers that are referred to herein as "lysosomal fusion-inhibitors". Lysosomal fusion-inhibitors are molecules that inhibit fusion of the target cell phagosome to the lysosome. Exemplary lysosomal fusion-inhibitors are the closely related class of glycolipids known as the anionic (e.g., multiacylated) trehalose glycolipids (referred to herein as "sulfatides") and the lectins (e.g., wheat germ agglutinin (WGA) and Concanavalin A (Con A). See, e.g., Goren, et al., *P.N.A.S. U.S.A.* 73:2510–2514 (1976)) and Hart, P. D. and M. R. Young, *Exp. Cell Res.* 118:365–375 (1979) for a discussion of exemplary fusion-inhibitors. In a preferred embodiment, the liposome contains from about five to about five to ten thousand molecules of the lysosomal fusion-inhibitor (preferably a sulfatide) per liposome. In a particularly preferred embodiment, the liposome contains from about five to about 500 molecules of the lysosomal fusion-inhibitor per liposome.

As noted above, the phrase "lysosomal fusion-inhibitor" refers to a compound that is capable of inhibiting (or delaying) fusion of the target cell phagosome to the lysosome. Screening assays for identifying putative lysosomal fusion-inhibitors are described in the Examples. The screening assays measure the ability of a putative lysosomal fusion-inhibitor to inhibit or delay movement of a labeled agent, such as a fluorescent-labeled agent or a radiolabeled agent) from a phagosome to a phagolysosome or lysosome. In general, lysosomal fusion-inhibitors are selected by preparing liposomes with candidate (putative) lysosomal fusion-inhibitors conjugated to the outer surface of the liposome and with, for example, fluorescein isothiocyanate-labeled bovine serum albumin (FITC-BSA) entrapped within the liposome. These liposomes are added to macrophages in vitro and the lysosomal degradation of FITC-BSA is measured by quantifying the generation of trichloroacetic acid (TCA)-soluble fluorescein. Liposomes that have been delivered to lysosomes rapidly convert FITC-BSA to TCA-soluble fluorescein. Agents which slow delivery to the lysosomes reduce or inhibit this response. The preferred lysosomal fusion inhibitors are the anionic trehalose glycolipids (sulfatides) as described in Goren, et al., P.N.A.S. U.S.A. 73:2510–2514 (1976).

The liposomes of the invention are useful for delivering an extracellular agent to the cytoplasm of a target cell. The extracellular agent is entrapped within the liposome in accordance with procedures well known to those of ordinary skill in the art. See, e.g., the Examples and U.S. Pat. Nos. 4,863,874, issued to Wassef et al.; 4,921,757, issued to Wheatley et al.; 4,925,661, issued to Huang; and 5,225,212, issued to Martin et al. Alternatively, or additionally, the liposomes can be delivered to the phagosome to render the phagosomal membrane permeable to agents that are already contained therein. For example, the liposomes of the invention (with or without extracellular agents entrapped therein) can be used to render the phagosomal membrane permeable to agents (i.e., phagosome-entrapped agents) that are already present in the phagosome. Such phagosome-entrapped agents may be the same or different from the extracellular agents that are entrapped within the claimed liposomes. According to this embodiment, the liposomes of the invention are used to facilitate the movement of phagosome-entrapped agents across the phagosomal membrane and into the cytoplasm, thereby rendering such pathogens more susceptible to conventional antibiotic or other therapy. Similarly, the liposomes of the invention are useful for facilitating the cytoplasmic delivery of molecules that arrive in endocytic compartments independently. In this manner, the delivery of any agent that is deliverable from inside a liposome is facilitated by the co-administration (concurrent or sequential administration) of the liposomes disclosed herein.

According to the preferred embodiments, the liposomes contain an extracellular agent that has an intracellular activity. The preferred extracellular agents are membrane impermeant peptides, oligonucleotides, nucleic acids (e.g., nucleic acid from which a useful RNA can be transcribed, nucleic acid encoding a peptide or protein (genes or cDNA), vectors (e.g., plasmids)), antibiotics (e.g., gentamycin, cephalosporins, penicillin, erythromycin), antimicotics, anti-viral agents, anti-cancer agents, enzymes, enzyme modulators (e.g., coenzymes, enzyme inhibitors), and imaging agents. The particularly preferred extracellular agents are peptides, oligonucleotides, nucleic acids and antibiotics. That some of the above-noted extracellular agents can have more than one intracellular function (e.g., an oligonucleotide, such as an antisense molecule, can function as an antiviral agent or an anti-cancer agent), would be immediately apparent to one of ordinary skill in the art.

The liposomes disclosed herein are useful in any application for which conventional liposomes currently are used.

The liposomes disclosed herein are particularly useful in all aspects of human therapeutic drug delivery, including gene therapy. Recently, the oncogene-repressing gene E1A (which represses the oncogene HER-2/neu that has been implicated in ovarian cancer) reportedly has been complexed to a cholesterol-based liposome vector and has been used successfully to treat a mouse model of ovarian cancer (BioWorld Today, American Health Consultants, Vol. 6(60), pages 1,3 (Mar. 29, 1995). Liposome vectors also have been reported in a Phase I clinical trial as an alternative to viral delivery of the cystic fibrosis genes (BioWorld Today, American Health Consultants, Vol. 6(3), pages 1,4 (Jan. 6, 1995) and Natasha Caplen et al., Nature Medicine Vol. 1 (January 1995), "Liposome-mediated CFTR gene transfer to the nasal epithelium of patients with cystic fibrosis." Exemplary liposome vectors for gene therapy are disclosed in International Patent Publication No. WO 95/03788 entitled "Liposomal Antisense Methyl Phosphonate Oligonucleotides and Methods for their Preparation and Use", claiming priority to U.S. patent application Ser. No. 08/099,229, filed Jul. 29, 1993 now U.S. Pat. No. 5,417,978, inventors A. M. Tari et al. and described in BioWorld Today, American Health Consultants, page 1 (Dec. 15, 1994).

Exemplary diseases which can be treated using the liposomes of the invention to deliver a gene to a target cell include, but are not limited to, cystic fibrosis, ovarian cancer, adenosine deaminase deficiency, sickle cell anemia, thalassemia, hemophilia, diabetes, alpha-antitrypsin deficiency, brain disorders such as Alzheimer's disease and brain tumors, and other illnesses such as growth disorders and heart diseases, for example, those caused by alterations in the way cholesterol is metabolized and defects of the immune system. See also U.S. Pat. No. 5,399,346, issued to W. French Anderson ("Gene Therapy") for a list of genes/disorders that can be administered/treated using gene therapy.

The liposomes disclosed herein advantageously provide a method for delivering membrane impermeant, extracellular agents to the cytoplasm of the target cells. As noted above, a "membrane impermeant extracellular agent" refers to an extracellular agent that cannot penetrate a cell membrane (e.g., plasma membrane, endosome membrane) at a level sufficient to mediate its intracellular activity. Thus, the claimed invention advantageously offers methods and compositions for delivering extracellular agents to the target cell cytoplasm which otherwise could not be so delivered. Exemplary membrane-impermeant, extracellular agents include peptides, proteins (particularly high molecular weight proteins), carbohydrates (monosaccharides and polysaccharides) and oligonucleotides. Peptides/proteins which modulate the macrophage inflammatory response (e.g., by interfering with the signaling mechanism for inflammation) are particularly preferred extracellular agents for entrapment in the liposomes disclosed herein.

Additional extracellular agents that can be delivered to target cells using the claimed liposomes include other types of proteins (e.g., apoproteins, glycoproteins, antigens and antibodies), haptens and antibodies thereto, receptors and other membrane proteins, protein analogs in which at least one non-peptide linkage replaces a peptide linkage, amino acids and their derivatives, hormones, lipids, phospholipids, liposomes that can be encapsulated by those of the invention; toxins such as aflatoxin, digoxin, xanthotoxin, rubratoxin; analgesics such as aspirin, ibuprofen, and acetaminophen; bronchodilators such theophylline and albuterol; beta-blockers such as propranolol, metoprolol, atenolol, labetolol, timolol, penbutolol, and pindolol; antimicrobial agents such as those described above and ciprofloxacin, cinoxacin, and norfloxacin; antihypertensive agents such as clonidine, methyldopa, prazosin, verapamil, nifedipine, captopril, and enalapril; cardiovascular agents including antiarrhythmics, cardiac glycodides, antianginals and vasodilators; central nervous system agents including stimulants, psychotropics, antimanics, and depressants; antiviral agents; antihistamines such as chlorpheniramine and brompheniramine; cancer drugs including chemotherapeutic agents; tranquilizers such as diazepam, chordiazepoxide, oxazepam, alprazolam, and triazolam; anti-depressants such as fluoxetine, amitriptyline, nor-triptyline, and imipramine; H-2 antagonists such as nizatidine, cimetidine, famotidine, and ranitidine; anti-convulsants; antinauseants; prostaglandins; muscle relaxants; anti-inflammatory substances; stimulants; decongestants; antiemetics; diuretics; antispasmodics; antiasthmatics; anti-Parkinson agents; expectorants; cough suppressants; mucolytics; vitamins; and mineral and nutritional additives. Extensive lists of these and other extracellular agents having an intracellular activity are provided in Remington's Pharmaceutical Science, 18th edition, ed. A. Gennaro, Mack Publishing Co., Eaton, Pa. (1990).

Other exogenous agents that can be used in accordance with the invention include peptides or proteins that interfere with inflammation (e.g., interleukin-1 beta converting enzyme (ICE) antagonists), the art-recognized and biologically functional analogs and derivatives of nucleotides and oligonucleotides including, for example, methylated polynucleotides and nucleotide analogs having phosphorothioate linkages; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes; promoters; enhancers; inhibitors; and other ligands for regulating gene transcription and translation.

The liposomes disclosed herein can be used to deliver the extracellular agent to an intracellular location (e.g., phagosome, cytoplasm) of the target cell. The intracellular location contains an intracellular structure (e.g., a microorganism, one or more proteins responsible for antigen processing, a nucleic acid) with which the extracellular agent specifically interacts to mediate the intracellular function of the extracellular agent. Exemplary target cells include macrophages, neutrophils, endothelial cells, fibroblasts, B-cells, T-cells, monocytes and tumor cells corresponding to these and other cells. Macrophages are the preferred target cells. If the liposomes are to be delivered to target cells in vivo, the liposomes typically are placed in a pharmaceutically acceptable carrier (e.g., standard saline solution) prior to administration. Exemplary pharmaceutically acceptable carriers for liposomes are well known to those of ordinary skill in the art. See, e.g., U.S. Pat. No. 5,225,212, issued to Martin et al.

According to one particularly preferred embodiment, the extracellular agent is an antibiotic, a peptide, an oligonucleotide or a nucleic acid that is useful for treating a disease attributable to an intracellular microorganism. Exemplary diseases that are attributable to an intracellular microorganism include typhoid fever, Legionnaire's disease, tuberculosis, leishmaniasis, histoplasmosis, candidiasis, Mycobacterium avium complex and Salmonellosis. Antibiotics that are known to be useful for treating the foregoing diseases include amphotericin B, amikacin, gentamycin and ampicillin. Each of these antibiotics can be entrapped within the liposomes disclosed herein for delivery to an intracellular location of a target cell.

In a particularly preferred embodiment, the extracellular agent is an antibiotic and the invention is used to deliver the antibiotic to the cytoplasm of cells in vivo or in vitro and/or to facilitate the killing of phagosome-entrapped bacteria by rendering the phagosomes which harbor the bacteria, permeable to the bacteria and/or to the antibiotic. Bacterial contamination of cells in culture is a problem frequently associated with large scale production of recombinant proteins. Although cells in culture can be treated with relatively large doses of antibiotic, such treatment is ineffective at eliminating the bacteria that reside within the phagosomes of the cells. The invention overcomes the problem of intracellular bacterial compartmentalization by providing a liposome that initially delivers the antibiotic to the target cell phagosomes and thereafter, to the target cell cytoplasm. Accordingly, for an in vitro antibiotic application, the liposome-entrapped antibiotic is substituted for the free antibiotic and is used in accordance with standard practice for delivering a liposome to cells in culture. For an in vivo application, the liposome-entrapped antibiotic is placed in a pharmaceutically acceptable carrier and is administered in accordance with standard procedures known to those of ordinary skill in the art of liposome drug delivery. Thus, the invention also embraces a method for manufacturing a pharmaceutical composition for delivering an extracellular agent to a cell in vivo, which method involves placing the above-described liposome (containing the antibiotic or other therapeutically useful agent) in a pharmaceutically acceptable carrier.

According to yet another preferred embodiment, the extracellular agent is an oligonucleotide and the liposomes disclosed herein are used to deliver the oligonucleotide to the cell cytoplasm, for example, to affect in vitro or in vivo transcription or translation within the target cell. The liposomes can be used, for example, to deliver an antisense RNA that is capable of hybridizing to a target cell or other nucleic acid, to modulate transcription (or translation) of selected target cell or other nucleic acid sequences. As described above with respect to antibiotic delivery, the oligonucleotides can be entrapped within the liposomes of the invention and used to deliver the oligonucleotides to an intracellular location (e.g., phagosome, cytoplasm) in accordance with routine procedures known to one of ordinary skill in the art of liposome drug delivery. Particularly preferred oligonucleotides for administration in accordance with the methods of the invention are antisense oligonucleotides which specifically inhibit HIV replication and/or transcription.

According to another particularly preferred embodiment, the exogenous agent is a peptide or protein and the liposomes disclosed herein are used to deliver the peptide/ protein to the target cell cytoplasm. Once in the cytoplasm, the peptide/protein can interact, for example, with one or more proteins or other intracellular structures that are responsible for processing antigens for presentation in association with the major histocompatibility complex (MHC) molecules. Exemplary proteins that can be delivered for MHC class I-restricted antigen presentation include viral, bacterial, or protozoan antigens, proteins and/or peptides. In contrast to the prior art vaccines (which are class II molecule vaccines), the present invention provides methods and compositions for the preparation of class I MHC vaccines.

According to yet another aspect of the invention, methods and compositions for delivering an exogenous agent to a target cell in vivo are provided. One method involves administering a pharmaceutical composition containing a therapeutically effective amount of the liposomes of the invention. Preferably, the therapeutically effective amount is between about 1 ug and about 100 mg/kg. The liposomes are formulated into a pharmaceutical composition by combination with an appropriate pharmaceutically acceptable carrier in accordance with routine procedures known to one of ordinary skill in the art. See, e.g., U.S. Pat. No. 5,225,212, issued to Martin et al. The liposomes may be used alone or in appropriate association, as well as in combination with other pharmaceutically active compounds. The liposomes may be formulated into preparations in solid, semisolid, or liquid form such as tablets, capsules, powders, granules, ointments, solutions, suppositories, and injections, in usual ways for topical, nasal, oral, parenteral, or surgical administration. Exemplary pharmaceutically acceptable carriers for liposomes are described in U.S. Pat. Nos. 5,225,212, issued to Martin et al., and International Patent Publication No. WO 95/03788, claiming priority to U.S. application Ser. No. 08/099,229, filed Jul. 29, 1993, inventors A. M. Tari, et al., the entire contents of which patent/patent publication are incorporated herein by reference. In view of the foregoing, there is no reasonable basis upon which one of ordinary skill in the art would reasonably question that the above-referenced pharmaceutically acceptable carriers could be used to deliver the claimed liposomes.

The liposomes of the invention are useful for facilitating the transport of an extracellular agent across the membrane of a target cell and into an intracellular location, in particular, the target cell cytoplasm. According to one aspect of the invention, a method is provided which involves contacting the liposome (containing the extracellular agent) with the target cell for a time sufficient to permit internalization of the liposome by the target cell. The step of contacting the target cell with the liposome can be performed in vitro (e.g., the liposomes can be added to cells in culture, for example, to eliminate or reduce bacterial contamination) or in vivo.

The liposomes of the invention are particularly useful for delivering extracellular agents to cells in culture. According to this aspect of the invention, the cells are contacted with the liposomes of the invention in vitro for a period of time sufficient to permit internalization of the liposome by the target cell and preferably, for a period of time sufficient to permit transport of the extracellular agent from the target cell phagosome to the cytoplasm. Exemplary procedures for using the claimed liposomes to deliver an agent that is an antibiotic or an oligonucleotide to a target cell are provided in the Examples. In general, the methods of the invention for delivering the extracellular agent in vitro utilize art-recognized protocols for delivering the agent with the only modification being the entrapment of the extracellular agent in the liposomes of the invention and substituting the liposome-entrapped extracellular agent for the extracellular agent used in the art-recognized protocol. Exemplary vesicle-forming lipids and phagosomal membrane permeabilizers that are useful for forming the disclosed liposomes, as well as the extracellular agents that can be entrapped therein, are described above. In a particularly preferred embodiment, the extracellular agent is a detectable agent, i.e., an agent that can be detected using routine procedures and detection methods, e.g., fluorescence microscopy, so that transport of the liposome (containing the extracellular agent) into the target cell and/or transport of the extracellular agent into the cytoplasm can be monitored. Delivery of an extracellular agent to the target cell cytoplasm can be detected, for example, by loading a fluorescent dye into the liposomes, contacting the liposomes with the target cells, and measuring the appearance of dye in the nucleus of the cell using fluorescence microscopy. The delivery of extracellular agents for modulation of cell mediated immunity can be detected by, for example, measuring MHC class I-restricted antigen presentation, as described by Harding, C. V., in: Microbes as Tools for Cell Biology, ed., D. G. Russell, Academic Press, N.Y. (1994), pp. 313–326. The liposomes of the invention also are useful for delivering an extracellular agent to cells in vivo. According to this aspect of the invention, the liposomes are placed in a pharmaceutically acceptable carrier and are delivered to a mammalian recipient in accordance with known methods of liposome drug delivery. Such methods are described in the above-referenced U.S. Patents. An exemplary procedure for delivering an extracellular agent that is a therapeutic agent is provided in the Examples. In general, the methods of the invention for delivering an extracellular agent in vivo utilize art-recognized protocols for delivering liposomes and/or the particular extracellular agent, with the only modification being the substitution of the liposome-entrapped extracellular agent for the extracellular agent used in the art-recognized protocol.

The instant invention provides methods and compositions for facilitating the transport of a liposome-entrapped extracellular agent to the cytoplasm of a target cell and evaluating the extent of the transport. The following examples illustrate representative utilities of the instant invention.

EXAMPLES

I. Liposome Preparation

Improvements of pH-sensitive liposomes

In general, pH-sensitive liposomes are formed by incorporating vesicle-forming lipids that confer pH-sensitivity into liposomes (see, e.g., D. C. Collins, et al., *Biochim. Biophys. Acta* 1025:234–242 (1990)). The liposomes are made by a reverse-phase evaporation method, followed by 4 cycles of freeze-thawing and extrusion through polycarbonate filters (0.1 μm pore size). See also Olson, F. et al., *Biochim. Biophys. Acta.* 557:9–23 (1979) and Szoka, F. et al., *Biochim. Biophys. Acta.* 601:559–571 (1980). This produces liposomes with a mean diameter of about 110 nm. The average sizes of liposomes are varied using different pore-size filters for extrusion (0.05, 0.1, 0.2, 0.4 μm).

Liposomes composed of oleic acid plus phosphatidylethanolamine (PE), or cholesteryl hemisuccinate (CHEMS) plus PE, are stable at neutral pH but unstable at low pH (Chu, C.-J. et al., *Pharmaceut. Res.* 7:824–834 (1990); Lai, M.-Z. et al., *Biochemistry* 24:1654–1661 (1985)). Example Table 1, formulation G shows a pH sensitive liposome that is useful for forming the improved liposomes disclosed herein. Phagosomes acidify before fusing with lysosomes (McNeil et al., *J. Cell Biol.* 97:692–702 (1983)). When endocytosis delivers pH-sensitive liposomes into an acidic compartment, the liposomes become destabilized and release their contents. Accordingly, the pH-sensitive liposomes disclosed herein release their contents in the phagosome, prior to lysosome fusion. Although the efficiency of delivery for the prior art pH-sensitive liposomes reportedly has been relatively poor (Chu, C.-J. et al., *Pharmaceut. Res.* 7:824–834 (1990)), the novel liposomes disclosed herein offer improved properties for agent delivery into a target cell by combining pH-sensitivity with a mechanism for facilitating the transport of liposome-entrapped agents across the phagosomal membrane prior to lysosome fusion.

A. General Protocol

Liposomes are prepared from vesicle-forming lipids at neutral pH or in accordance with procedures known to one of ordinary skill in the art. The preferred procedure for making the liposomes is based on the reverse phase evaporation method described by Szoka and Papahadjopoulos (*Annu. Rev. Biophys. Bioengineering*, 1980) or by hydrating lipids and freeze-thawing. The liposomes are subsequently extruded under high pressure argon through polycarbonate membranes (Nuclepore, Pleasanton, Calif.) with a final pore size of 0.05–0.2 mm. HPTS or Calcein is encapsulated in the liposomes at 35 mM concentration with 10 mM HEPES buffer, and the unencapsulated material is removed by a gel filtration column. The concentration of phospholipid is routinely assayed by the method of Bartlett. Standard procedures, such as those described above and in the above-identified references, are used for the production of pH-sensitive liposomes. Exemplary vesicle-forming lipids are disclosed in the detailed description of the invention.

The procedure used to make the liposomes is presented herein.

The following compounds are dissolved in 2 ml of chloroform: phosphatidylcholine (10 µmol), phosphatidylserine (1 µmol) or $G_{M1}$ (1 µmol), cholesterol (5 µmol). This solution is evaporated under vacuum, using a rotating evaporator, until the chloroform is removed and the lipids coat the wall of a glass test tube. To this preparation is added 0.5 ml of an aqueous solution containing a fluorescent dye (calcein, for example) or other agent (for example, drug or protein) to be entrapped in liposomes. A representative solution would include 50 mM NaCl, 60 mM calcein and 10 mM HEPES, pH 7.4. This solution is then maintained at room temperature to hydrate the lipids. The resulting multilamellar vesicles are freeze-thawed 4 times using ethanol at −20° C. This solution is then passed 4 times through an automated or manual extruder, using 0.2 µm (or smaller) pore size filters; effectively converting the phospholipid vesicles into unilamellar vesicles (liposomes) with more uniform size range. Unencapsulated molecules are then removed from the liposomes by gel permeation chromatography, using Sephadex G25 resin and running in phosphate-buffered saline. When calcein has been encapsulated into the liposomes, the chromatography shows an elution profile containing two fluorescent peaks; the first being the calcein enclosed in liposomes, the second being the extraliposomal calcein. The first peak is saved as the preparation of liposomes.

Example Table 1
Liposomes to be Tested for Delayed Progression

| A. | PC, containing FDx10 or HPTS |
| B. | PC/PS, containing FDx10 or HPTS |
| C. | PC/PI, containing FDx10 or HPTS |
| D. | PC/CHEMS, containing FDx10 or HPTS |
| E. | PC/$G_{M1}$, containing FDx10 or HPTS |
| F. | PC/sulfatide, containing FDx10 or HPTS |
| G. | PC/PE/oleic acid, containing calcein[a]; or PC/PE/CHEMS[a] containing calcein[a] |

[a]For pH-sensitive liposomes (G), some or all of the PC in liposome formulations A–F is replaced with phosphatidylethanolamine (PE), and oleic acid or CHEMS is incorporated.

B. Preparation of pH-sensitive Liposomes

The preparation of pH-sensitive liposomes is described in, for example, U.S. Pat. No. 4,925,661, issued to Huang. In general, pH-sensitive liposomes are prepared in accordance with the above-described general protocol for forming liposomes with the modification that the liposome formulations further contain at least one pH-sensitive lipid. Exemplary pH-sensitive lipids are disclosed in the detailed description of the invention.

C. Preparation of Liposomes containing a Phagosomal Membrane Permeabilizer

Hemolysins are the preferred phagosomal membrane permeabilizers. Hemolysins are expressed by diverse species of gram-positive bacteria. They are soluble proteins that bind to membranes and oligomerize to form membrane pores. Among them, Listeriolysin O (LLO) from *Listeria monocytogenes* has been shown to have a sharp pH profile of hemolytic activity, optimal at pH 5.5 (Portnoy, D. et al., *Infect. and Immun.* 60:2710–2717 (1992)). LLO is encapsulated inside pH-sensitive (or pH-insensitive) liposomes as described below. The LLO leaks out of the liposomes upon destabilization of the bilayer at the endosomal (phagosomal) pH 6.0, binds to the phagosomal membrane, and creates membrane pores that permit other liposome contents, such as fluorescein-labeled dextran (FDx) or 8-hydroxy-1,3,6-pyrene-trisulfonate (HPTS), to enter the cytoplasm. To increase the stability of LLO-containing liposomes at neutral pH, cholesterol is excluded from or is present at a reduced concentration in the liposome bilayer and/or the aqueous compartment of the liposome is strongly buffered. Under ordinary liposome-forming conditions, the LLO-containing liposomes disclosed herein are stable for at least one week.

*L. monocytogenes* strain L1545 was incubated at 37° C. in 300 ml TGY broth medium and subcultured for 16 hours with continuous shaking. (TGY broth medium contains 80 g of Yeast Extract, 120 g of Trypticase, 13.17 Na2HPO4, and 2.8 g KH2PO4 in 4 liters, pH 7.5 with additional 0.1 mM ZnSO4 and 1% D-Glucose and 8 gm activated charcoal). 55 ml of overnight subculture was additionally cultured in 600 ml TGY medium for 9 hours at 37° C. with continuous shaking. The culture was spun at 8000 rpm for 15 min in a GSA rotor (Sorvall RC5). Bacteria and charcoal were spun out and the supernatant was filtered through 0.45 um pore size filter. The supernatant was concentrated to 150 ml by Minitan (Millipore) tangential flow concentrator and the buffer was changed to 20 mM Tris-HCl pH 7.4 during this concentration. Then the concentrate was run through Q-Sepharose anion exchange column (Pharmacia, 26/40 Column dimension) preequilibrated with 20 mM Tris-HCl, pH 7.4 and the flow through was collected. The flow through was concentrated again to 10 ml and LLO was further purified by gel filtration sizing column (Sephacryl S200) using phosphate buffered saline containing 10% glycerol. The fraction containing 58 kD molecular weight protein was collected and pooled.

The above-described general protocol for forming a liposome is used for forming a pH-sensitive liposome containing a phagosomal membrane permeabilizer (a hemolysin) with the following modification: the liposome formulation further includes 1 mg/ml LLO (or other membrane permeabilizing agent) in the hydration phase. Optionally, the liposome formulation further includes extracellular agents in the hydration phase for entrapping such agents in the lumens of the liposomes for delivery to the cytoplasm of a target cell. As would be apparent to one of ordinary skill in the art, the exemplary procedure can be modified using no more than routine skill and experimentation to form pH-sensitive and pH-insensitive liposomes containing a variety of vesicle-forming lipids and phagosomal membrane permeabilizers.

The particular protocol used to prepare the LLO-containing liposomes disclosed herein is presented below.

pH-sensitive, LLO-containing liposomes are prepared using methods similar to those for making standard, non-LLO-containing liposomes, replacing some of the lipids with other compounds and adding LLO to the aqueous phase. The following compounds are dissolved in 2 ml of chloroform: phosphatidylethanolamine (10 µmol), cholesteryl hemisuccinate (5 μmol). After evaporation, 0.5 ml of an aqueous solution (1 mg/ml LLO, 50 mM NaCl, 60 mM calcein and 10 mM HEPES, pH 7.4) is added to the container. The preparation is freeze-thawed, extruded and separated by gel permeation chromatography, using Sepharose CL resin, as described.

As would be apparent to one of ordinary skill in the art, the substitution of any vesicle-forming lipid for the particular vesicle-forming lipid used in the example can be made to make a pH-sensitive lipid which includes different lipids and/or a different phagosomal membrane permeabilizer than those used in the specific example. Thus, the foregoing protocol can be used to prepare pH-sensitive, as well as pH-insensitive liposomes which include a phagosomal membrane permeabilizer.

D. Preparation of Liposomes further including a Lysosome Fusion-inhibitor

An exemplary procedure for forming a pH-sensitive, phagosomal membrane permeabilizer-containing liposome that further includes an exemplary lysosome fusion-inhibitor (a sulfatide) is described herein. As would be apparent to one of ordinary skill in the art, the exemplary procedure can be modified using no more than routine skill and experimentation to form pH-sensitive and pH-insensitive liposomes containing a variety of vesicle-forming lipids, phagosomal membrane permeabilizers and lysosome fusion-inhibitors.

The procedure for forming a pH-sensitive liposome containing a sulfatide is as follows.

pH-sensitive, LLO-containing liposomes with sulfatides are prepared using methods similar to those for making pH-sensitive, LLO-containing liposomes; the only difference being the composition of the lipid mixture used to make the liposomes. The following compounds are dissolved in 2 ml of chloroform: phosphatidylethanolamine (10 μmol), cholesteryl hemisuccinate (5 μmol), 2,3,6,6'-tetraacyl trehalose 2'-sulfate (a representative sulfatide)(1 μmol). Other procedures are identical to those described above.

E. Preparation of Liposome-entrapped Extracellular Agent

An exemplary procedure for forming a pH-sensitive, phagosomal membrane permeabilizer-containing liposome that further includes an extracellular agent (a fluorescent dye) is described herein. The procedure is based on the above-described general protocol for forming the liposomes with the modification that calcein at 1 to 10 mg/ml is included in the aqueous phase in the presence or absence of LLO (at 1 mg/ml as described above). Unloaded calcein and LLO are removed by gel permeation chromatography.

As would be apparent to one of ordinary skill in the art, various extracellular agents can be entrapped within the liposomes of the invention by substituting the extracellular agent of interest for the fluorescent dye in the above-described protocol. Exemplary extracellular agents that are suitable for liposome entrapment are disclosed in the detailed description of the invention.

F. Preparation of Surface-modified Liposomes

The liposome surface is modified by incorporating therein or conjugating thereon various proteins that are selected to change the rate of liposome binding to the cell surface and/or progression to the lysosome. IgG, transferrin, wheat germ agglutinin (WGA) and/or concanavalin A are coupled to the liposome surface according to methods known to those of ordinary skill in the art (e.g., Bogdanov, A. et al., *Exp. Cell Res.* 181:362–374 (1989)); Hutchinson, F. et al., *Biochim. Biophy. Acta.* 978:17–24 (1989), and the kinetics of liposome delivery to lysosomes and the release of liposome-entrapped agents are determined. The proteins are selected to result in a surface-modified liposome which is ingested by the target cell but which does not fuse with lysosomes (or fuses at a slower rate than a liposome which has not been subjected to surface modification).

Two categories of modified liposomes are synthesized, and their rates of progression to lysosomes are compared to that of IgG-coated liposomes (which should exhibit the fastest rate of delivery to the lysosomes). The IgG-coated liposomes are formed by standard procedures such as those described by A. A. Bogdanov, et al. in *Exp. Cell Res.* 181:362–374 (1989). The surface-modified liposomes described below exhibit altered intracellular routes and/or rates of progression through the endocytic compartments of target cells. Example Table 2 discloses the types of modifications that are made to characterize the effect of liposome surface modification on liposome progression.

Example Table 2
Surface Modulations that Delay or Accelerate Progression

| | |
|---|---|
| H. | Formulations A–G, with conjugated wheat germ agglutinin |
| I. | Formulations A–G, with conjugated concanavalin A |
| J. | Formulations A–G, with conjugated transferrin |
| K. | Formulations A–G, with conjugated rabbit IgG. |

The first category of surface-modified liposomes is exemplified by a transferrin surface-modified liposome, formed by opsonizing a liposome with the transferrin. Transferrin is known to move freely within cells. Accordingly, the transferrin surface-modified liposomes enter early endosomes (phagosomes) but not late endosomes or lysosomes.

The second category of surface-modified liposomes is exemplified by a lectin (concanavalin A or wheat germ agglutinin) surface-modified liposome, formed by opsonizing a liposome with the lectin. Because lectins bind readily to macrophages without entering them or enter but exhibit delayed fusion with lysosomes (Edelson, P and Z. Cohn, *J. Exp. Med.* 140:1364–1386 (1974); Rabinowitz, S. et al., *J. Cell Biol.* 116:95–112 (1992)), the lectin surface-modified liposomes exhibit a similar progression within a target macrophage or other target cell as that reported for lectins alone.

Liposomes with molecules conjugated to their outside surface are prepared using standard liposome formulations, adding a phospholipid that contains a reactive group such as N-[4-(p-maleimidophenyl)butyryl]phosphatidylethanolamine (2 mol % of total phospholipid) for chemical cross-linking to added macromolecules. Macromolecules such as transferrin (1 mg/ml) are conjugated by adding to liposomes at pH 5.5 (Buffer: 120 mM NaCl, 10 mM MES, pH 5.5). Unconjugated molecules are removed by gel permeation chromatography, using Sepharose CL resin. The maleimide group is deactivated by adding a 2-fold molar excess of reducing reagent.

II. Liposome Characterization

A. Assay of Liposome Delivery to Lysosomes

For initial screening, liposomes of a given size profile having varied surface properties are studied. The liposomes for analysis contain aqueous content markers such as fluorescein-labeled dextran (FDx), 8-hydroxy-1,3,6-pyrenetrisulfonate (HPTS) or the fluorescent molecule calcein entrapped (encapsulated) therein. Surface properties of liposomes are varied by changing the lipid composition or by attaching other molecules (Example Tables 1 and 2). The liposomes are made by a reverse-phase evaporation method as described above, followed by 4 cycles of freeze-thawing and extrusion through polycarbonate filters (0.1 μm pore size). See also Olson, F. et al., *Biochim. Biophys. Acta.* 557:9–23 (1979) and Szoka, F. et al., *Biochim. Biophys. Acta.* 601:559–571 (1980). This produces liposomes with a mean diameter of about 110 nm. The average sizes of liposomes are varied using different pore-size filters for extrusion (0.05, 0.1, 0.2, 0.4 µm). Unencapsulated aqueous content markers (FDx, HPTS, and calcein) are removed using a Sephadex gel filtration column.

Fusion of liposome-containing phagosomes with lysosomes is monitored by a fluorescence microscopic method in which the distributions of one fluorophore restricted to lysosomes and a different fluorophore (e.g., calcein) encapsulated inside the liposomes are examined. Colocalization of the fluorophores after endocytosis of liposomes is indicative of delivery of liposomes into lysosomes. The lysosomal degradation of FITC-BSA contained in liposomes also can be measured as described above as an indication of liposome delivery into lysosomes.

Macrophages are exposed to FDx-containing liposomes for 5 min to allow phagocytosis, washed and chased for 5, 10, 15, 20, or 30 min with chase medium (i.e., buffer only). Fusion of phagosomes with lysosomes usually occurs within minutes of phagocytosis (Knapp, P. and J. Swanson, *J. Cell Sci.* 95:433–439 (1990)). Accordingly, the selected chase times should be sufficient to allow phagosome-lysosome fusion. Cells are then fixed, extracted and prepared for immunofluorescent localization of lysosomal glycoprotein-A (LGP-A), a lysosomal membrane glycoprotein, the presence of which in a phagosome is an indicator of phagosome-lysosome fusion. The chase time required for half-maximal colocalization of FDx-liposomes and LGP-A, i.e., the time at which half of the phagosomes have fused with lysosomes, is determined.

The foregoing method for assessing delivery of liposomes into lysosomes can be confirmed by electron microscopic (EM) techniques. For liposomes with encapsulated colloidal gold particles (~5 nm) (Huang, K. et al., *Biochim. Biophys. Acta.* 1069:117–121 (1991); Huang, S. et al., *Cancer Res.* 52:5135–5143 (1992)), electron microscopic measurements are used. For example, BSA complexes with 16 nm gold particles are preloaded by endocytosis and used as markers for lysosomes. Phagosome-lysosome fusion is quantified by fixing cells at various times after phagocytosis of gold-labeled liposomes, then quantifying by EM the number of vesicles containing both small (5 nm) and large (16 nm) gold (Rabinowitz, S. et al., *J. Cell Biol.* 116:95–112 (1992)). The various combinations of liposome phagocytosis times and chase time are modeled after the above-described studies using fluorescence microscopy.

B. Assay of Liposome Rupture inside Phagosomes

A second assay is used to measure the kinetics of liposome rupture inside endocytic compartments. The second assay is independent of phagosome delivery into lysosomes. The liposomes for this study contain concentrations of FDx that are sufficient to quench the fluorescence of fluorescein. Cells are plated onto cover slips that are designed to fit into a spectrofluorometer cuvette and are pulse-labeled 5 min with the FDx-containing liposomes to allow phagocytosis, then immediately assembled into the cuvette in the fluorometer. Cellular fluorescence is monitored in the fluorometer by exciting fluorescein at its pH-insensitive wavelength (450 nm). Degradative or pH-dependent rupture of the liposome results in release of the FDx from its liposome into the surrounding phagosome. This dilutes the FDx, reducing its self-quenching, and increasing its fluorescence. The kinetics of this fluorescence increase (i.e., the rate of increase of the detected fluorescence) indicates the kinetics of liposome rupture inside the phagosomes.

C. Assay for measuring pH-sensitivity and stability of LLO-containing liposomes

Each liposome formulation is tested for its pH-sensitivity spectrofluorometrically by measuring the release of encapsulated calcein. The liposomes contain a phagosomal membrane permeabilizer and a self-quenching concentration of calcein. Preferably, the phagosomal membrane permeabilizer is LLO. Calcein has been used for the in vitro assay of leakage by pH-sensitive liposomes because its permeability through intact bilayers is constant over a wide range of pH (Straubinger, R. et al., *Cell* 32:1069–1079 (1983)). Calcein quenched fluorescence is relieved (i.e., its fluorescence increases) upon dilution when it is released from liposomes. This assay can be used to monitor the stability of liposome formulations over a long (at least several months) period of time. Liposome stability is measured by loading liposomes with self-quenching concentrations of calcein, that is, the liposomes are relatively non-fluorescent. As the liposomes become unstable, lyse and release their contents, the internal calcein concentration decreases and its fluorescence increases.

D. Assay for measuring the Molecular Size Dependence of the Liposome Delivery System Different sizes of fluorescent probes are loaded into phagosomal membrane permeabilizer-containing liposomes (e.g., LLO-liposomes) to measure the molecular size-dependence of the liposome delivery system. Fluorescein dextran is available in sizes ranging from an average molecular weight 4,000 to 150,000. HPTS can be used as an indicator for smaller molecules (m.w. 550). Liposomes loaded with different sizes of fluorophore are provided to macrophages for phagocytosis, then the cells are measured for their differential extractability in saponin and Triton X-100. A measure of the efficiency of delivery by LLO-liposomes to the target cell is obtained as a function of the molecular size of the entrapped fluorescent probe.

E. Assays for measuring Delivery of Liposome Content (extracellular agent) into a Target Cell Cytoplasm The delivery of liposomal content into the cytoplasm is assayed by measuring detergent-releasable fluorescence from a target cell (e.g., a macrophage). FDx or HPTS is encapsulated inside liposomes as an aqueous content marker. Extraction of cells with the detergent saponin releases only cytoplasmic FDx, whereas extraction with the detergent Triton X-100 releases all intracellular FDx. If FDx has leaked out of liposomes but has remained in the phagosomal compartment, it will not be released by saponin treatment, but it will be released by Triton X-100 treatment. A successful delivery of liposomal content (extracellular agent content) into the cytoplasm can therefore be monitored by an increase in the ratio of saponin-extractable FDx to total intracellular FDx (Triton-releasable). If necessary, FDx from the surface-bound liposomes can be released by washing with a low pH buffer. As a positive control, FDx is scrape-loaded into the cytoplasm of cells (Swanson, J. et al., *J. Cell Biol.* 115:941–948 (1991); Swanson, J. et al., *Science* 238:548–550 (1987)). The ratio of saponin-extractable FDx to Triton-extractable FDx is maximal for this positive control. In this manner, the assays disclosed herein can be used as screening assays to select putative phagosomal membrane permeabilizers and lysosome fusion inhibitors for use in accordance with the methods and compositions of the invention.

Alternatively or additionally, delivery to the cytoplasm of the target cell of an extracellular agent that is an antibiotic is measured by observing the ability of the liposome-entrapped antibiotic agent to rescue macrophages infected with an intracellular parasite. For example, liposome-entrapped gentamycin is used to rescue macrophages that have been infected with Listeria monocytogenes, a pathogen which resides in the cytoplasm of the macrophages. The efficacy of liposome-entrapped antibiotic induced *L. monocytogenes* death is determined using assays that are known to those of ordinary skill in the art. See, e.g., Portnoy, et al., *Infect. Immun.* 60:2710–2717 (1992). Other exemplary antibiotics (and the pathogens which they treat) which can be used in accordance with this assay and/or the claimed compositions and methods of the invention are described in the detailed description of the invention.

The dose dependency of the encapsulated drug is compared with free (non-liposome entrapped) drug and/or with drug encapsulated inside conventional liposomes, such as the PC/PS formulation (Example Table 1). For each condition, a median lethal dose for killing *L. monocytogenes* ($LD_{50}$) is documented using a bacterial plating assay. Macrophages are infected with *L. monocytogenes* for 20 minutes, washed and chased for 1, 3, or 5 hours in the presence of (a) 10 μM gentamycin, (b) gentamycin encapsulated in PC/PS liposomes, and © gentamycin encapsulated in the liposomes disclosed herein. The loss of bacterial viability is quantified with respect to incubation time using routine procedures known to one of ordinary skill in the art, varying both the dose of *L. monocytogenes* and the dose of liposomes.

A further exemplary method for measuring the delivery of liposome-entrapped extracellular agent to the cytoplasm of a target cell involves measuring gene expression following delivery of a liposome-entrapped plasmid to a target cell. The plasmid includes a gene under the control of a promoter. Expression of the gene in the target cell is determined according to procedures known to those of ordinary skill in the art. See, e.g., Molecular Cloning, 2nd edition, Ed. J. Sambrook et al., Cold Spring Harbor Press, Cold Spring Harbor, N.Y. (1989). Exemplary genes for use in accordance with this assay and/or the claimed composition and methods of the invention are described in the detailed description of the invention. Published methods for measurement of MHC class I-restricted antigen presentation of ovalbumin can be used as a way of measuring protein delivery into cytoplasm (see, e.g., Harding, C. V. in *Microbes as Tools for Cell Biology*, ed. D. G. Russell, Academic Press, New York, N.Y. pp.313–326 (1994)).

The above-described in vitro assays for measuring delivery of a liposome-entrapped extracellular agent to the phagosome or cytoplasm of a target cell are recognized by those of ordinary skill in the art as predictive of the ability of the liposome to deliver its contents in vivo. See, e.g., (Düzgünes, N. et al., *Antimicrobial Agents and Chemotherapy* 32:1404–1411 (1988)) which describes the in vivo experiments for characterizing liposome-encapsulated amikacin in *Mycobacterium avium*-M. intracellular-infected mice that were based upon an in vitro mouse macrophage model.

Mouse macrophages serve as appropriate models for human macrophage biology. This is because the process of phagosome-lysosome fusion is fundamentally similar in mouse and human macrophages. In addition, the interactions between *Salmonella typhimurium* and mouse macrophages are similar to those between *S. typhi* and human mononuclear phagocytes. Moreover, the development of liposomes is best done using a murine system, as efficacy can be tested in whole-animal studies. The most promising methods and technologies developed using mouse macrophages are easily examined in human monocyte-derived macrophages.

Assessment of the uptake of various types of liposomes by different cell types is accomplished by using two fluorescent liposome markers, 8-hydroxy-1,3,6-pyrenetrisulfonate (HPTS), encapsulated inside the liposome lumens, and rhodamine-labeled phosphatidylethanolamine (Rho-PE), incorporated into the liposome bilayer. The extent of uptake has been found to depend both on the surface properties of the liposome (i.e., phospholipid headgroups) and on the type of cell ingesting the liposome (Lee, K.-D. et al., *Biochim. Biophys. Acta.* 1103:185–197 (1992); Lee, K.-D. et al., *Biochemistry* 32:889–899 (1993)). The Murine macrophage-like cell line J774 and human peripheral blood monocyte/macrophages have been compared with CV1 cells, an African green monkey kidney cell line. Uptake of liposomes in vitro correlated with the in vivo liposome clearance from blood by mononuclear phagocytic cells of the liver and spleen (K.-D. Lee and D. Papahadjopoulos (1995), Interaction of liposomes with cells in vitro in *Trafficking of Intercellular Membranes*, ed. M. C. Redroso de Lima, H. Duzgunes, D. Hoekstra springer-Verlag, Heidelberg, Germany). Methods for labeling the liposome lumen with colloidal gold particles and using those liposomes for imaging at both the EM and light microscopic level also have been reported (Huang, K. et al., *Biochim. Biophys. Acta.* 1069:117–121 (1991); Huang, S. et al., *Cancer Res.* 52:5135–5143 (1992)). Using a silver-enhancement method, liposomes have been localized in situ, inside macrophages of liver and spleen in mice and the sites of liposome uptake in solid tumors have been identified (Hong, K., et al., *Biochim. Biophys. Acta* 732:320–323 (1983) and Huang, S. K., et al., *Biochim. Biophys. Acta* 1069:117–121 (1991)).

The liposomes disclosed herein are administered in accordance with procedures known in the art for administering the prior art liposome formulations. For example, U.S. patent application Ser. No. 08/099,229 (corresponding to International Publication Number WO 95/03788) describes the formulation and administration of an improved liposome for performing gene therapy. Such procedures are known in the art and can be performed with no more than routine experimentation.

F. Liposomes that Delay Phagosome-lysosome Fusion

The normal kinetics of phagosome-lysosome fusion and of liposome rupture using conventional liposomes are assessed using the above-described procedures. Thereafter, the compositions of the liposomes of the invention are modified to increase uptake by macrophages and/or to slow the kinetics of phagosome-lysosome fusion (Example Table 1). Liposomes made of phosphatidylcholine (PC), PC plus phosphatidylserine (PS), PC plus phosphatidylinositol (PI), PC plus cholesteryl hemisuccinate (CHEMS), PC plus the ganglioside $G_{M1}$, and PC plus sulfatide glycolipid are initially examined to select a lysosomal fusion inhibitor for incorporation into liposomes containing phagosomal membrane permeabilizers. The charged components, PS, PI, and CHEMS included in the PC liposomes reportedly dramatically enhance uptake (Lee, K. et al., *Biochim. Biophys. Acta.* 1103:185–197 (1992)). Ganglioside-containing liposomes ($PC/G_{M1}$) reportedly reduce liposome uptake by macrophages, particularly in vivo (Papahadjopoulos, D. et al., *Proc. Natl. Acad. Sci. USA* 88:11460–11564 (1991)). Sulfatide, added to cells, reportedly inhibits phagosome-lysosome fusion (D'Arcy Hart, P. and M. Young, Exp. Cell Res. 118:365–375 (1979); Goren, M. et al., Proc. Natl. Acad. Sci. 73:2510–2514 (1976)). Accordingly, the Example Table 1 formulations B-D increase liposome uptake and formulations E and F delay phagosome-lysosome fusion. By combining these formulations, the optimal liposome compositions that are efficiently internalized but delivered slowly to lysosomes are obtained.

Each of the above-identified references, patents/patent publications is incorporated in its entirety herein by reference. The preceding is merely a detailed description of certain preferred embodiments. It therefore should be apparent to those skilled in the art that various modifications and equivalents can be made without departing from the spirit or scope of the invention.

What is claimed is:

1. A composition comprising a liposome consisting essentially of a plurality of vesicle-forming lipids, a bacterial hemolysin, and a therapeutic agent or diagnostic agent, wherein said bacterial hemolysin and said therapeutic agent or diagnostic agent are encapsulated within the lumen of said liposome.

2. The composition of claim 1, wherein a targeting molecule is attached to said liposome.

3. The composition of claim 1, wherein the liposome is a pH-sensitive liposome.

4. The composition of claim 3, wherein a targeting molecule is attached to said liposome.

5. The composition of claim 1, wherein at least one of the vesicle-forming lipids is selected from the group consisting of phosphatidylcholine, phosphatidylserine, phosphatidylinositol, phosphatidylglycerol, phosphatidic acid, monosialoganglioside (GM1), polyethylene glycol-phosphatidylethanolamine (PEG-PE), cholesterylhemisuccinate, phosphatidylethanolamine, oleic acid and cholesterol.

6. The composition of claim 5, wherein the vesicle-forming lipids comprise:

phosphatidylcholine in an amount ranging from about 5% to about 100% of the vesicle-forming lipid;

at least one lipid selected from the group consisting of phosphatidylserine, phosphatidylglycerol, phosphatidic acid and phosphatidylinositol in an amount ranging from about 0% to about 30% of the vesicle-forming lipid;

at least one lipid selected from the group consisting of GM1 and PEG-PE in an amount ranging from about 0% to about 30% of the vesicle-forming lipid; and cholesterol in an amount ranging from about 0% to about 50% of the vesicle-forming lipid.

7. The composition of claim 5, wherein the liposome is a pH-sensitive liposome having the composition:

at least one lipid selected from the group consisting of phosphatidylethanolamine and phosphatidylcholine in an amount ranging from about 50% to about 100% of the vesicle-forming lipid;

at least one lipid selected from the group consisting of cholesterylhemisuccinate and oleic acid in an amount ranging from about 0% to about 50% of the vesicle-forming lipid; and at least one lipid selected from the group consisting of phosphatidylserine, phosphatidylglycerol, phosphatidic acid, phosphatidylinositol, GM1 and PEG-PE in an amount ranging from about 0% to about 10% of the vesicle-forming lipid.

8. The composition of claim 1, wherein the therapeutic agent or diagnostic agent is selected from the group consisting of a peptide, an oligonucleotide, a nucleic acid, an antibiotic, an antimicotic, an anti-viral agent, an anti-cancer agent, an enzyme, an enzyme modulator and an imaging agent.

9. The composition of claim 4, wherein the therapeutic agent or diagnostic agent is selected from the group consisting of a peptide, an oligonucleotide, a nucleic acid, an antibiotic, an antimicotic, an anti-viral agent, an anti-cancer agent, an enzyme, an enzyme modulator and an imaging agent.

10. The composition of claim 1, wherein the therapeutic agent is useful for treating a disease attributable to an intracellular microorganism.

11. The composition of claim 10, wherein the disease attributable to the intracellular microorganism is selected from the group consisting of typhoid fever, Legionnaire's disease, tuberculosis, leishmaniasis, histoplasmosis, candidiasis, *Mycobacterium avium* complex and Salmonellosis.

12. The composition of claim 8, wherein the antibiotic is selected from the group consisting of amphotericin B, amikacin, gentamycin and ampicillin.

13. The composition of claim 1, wherein the bacterial hemolysin is listeriolysin O.

14. The composition of claim 4, wherein the bacterial hemolysin is listeriolysin O.

15. The composition of claim 13, wherein the liposome contains between about five and about one-hundred molecules of the bacterial hemolysin per liposome.

16. The composition of claims 1 or 4, further comprising a pharmaceutically acceptable carrier.

17. A method for facilitating the intracellular release in a target cell of a liposome-entrapped therapeutic agent or diagnostic agent, the method comprising:

entrapping a selected therapeutic agent or diagnostic agent within a lumen of a liposome formed of vesicle-forming lipids to form the liposome-entrapped therapeutic agent or diagnostic agent, the lumen of the liposome further including a bacterial hemolysin, and contacting the target cell with the liposome-entrapped therapeutic agent or diagnostic agent for a time sufficient to permit internalization of the liposome by the target cell.

18. A method for facilitating the intracellular release in a target cell of a liposome-entrapped therapeutic agent or diagnostic agent, the method comprising:

entrapping a selected therapeutic agent or diagnostic agent within a lumen of a liposome formed of vesicle-forming lipids to form the liposome-entrapped therapeutic agent or diagnostic agent, the liposome including a lysosomal fusion-inhibitor, the lumen of the liposome further including a bacterial hemolysin, wherein the lysosomal fusion-inhibitor is selected from the group consisting of a sulfatide and a lectin, and contacting the target cell with the liposome-entrapped therapeutic agent or diagnostic agent for a time sufficient to permit internalization of the liposome by the target cell.

19. The method of claim 17 or claim 18 wherein the step of contacting the target cell with the liposome-entrapped therapeutic agent or diagnostic agent is performed in vitro.

20. The method of claim 19, wherein the step of contacting the target cell with the liposome-entrapped therapeutic agent or diagnostic agent comprises adding the liposome to a cell culture.

21. The method of claim 17 or claim 18, wherein the step of contacting the target cell with the liposome-entrapped therapeutic agent or diagnostic agent is performed in vivo.

22. The method of claim 17 or claim 18, wherein the therapeutic agent or diagnostic agent is selected from the group consisting of an antibiotic, a peptide, an oligonucleotide and a nucleic acid.

23. A method for facilitating the release in a target cell of phagosome-entrapped agents from phagosomes, the method comprising:

contacting the target cell with a liposome having a lumen and including a bacterial hemolysin encapsulated within the lumen for a time sufficient to permit phagocytosis of the liposome by the target cell.

24. A composition comprising a liposome consisting essentially of a plurality of vesicle-forming lipids and a bacterial hemolysin contained within the lumen of said liposome.

25. The composition of claim 24, wherein the liposome is a pH-sensitive liposome.

26. The composition of claim 24, wherein at least one of the vesicle-forming lipids is selected from the group consisting of phosphatidylcholine, phosphatidylserine, phosphatidylinositol, phosphatidylglycerol, phosphatidic acid, monosialoganglioside (GM1), polyethylene glycol-phosphatidylethanolamine (PEG-PE), cholesterylhemisuccinate, phosphatidylethanolamine, oleic acid and cholesterol.

27. The composition of claim 26, wherein the vesicle-forming lipids comprise:

phosphatidylcholine in an amount ranging from about 5% to about 100% of the vesicle-forming lipid;

at least one lipid selected from the group consisting of phosphatidylserine, phosphatidylglycerol, phosphatidic acid and phosphatidylinositol in an mount ranging from about 0% to about 30% of the vesicle-forming lipid;

at least one lipid selected from the group consisting of GM1 and PEG-PE in an amount ranging from about 0% to about 30% of the vesicle-forming lipid; and cholesterol in an amount ranging from about 0% to about 50% of the vesicle-forming lipid.

28. The composition of claim 26, wherein the liposome is a pH-sensitive liposome having the composition:

at least one lipid selected from the group consisting of phosphatidylethanolamine and phosphatidylcholine in an mount ranging from about 50% to about 100% of the vesicle-forming lipid;

at least one lipid selected from the group consisting of cholesterylhemisuccinate and oleic acid in an amount ranging from about 0% to about 50% of the vesicle-forming lipid; and at least one lipid selected from the group consisting of phosphatidylserine, phosphatidylglycerol, phosphatidic acid, phosphatidylinositol, GM1 and PEG-PE in an amount ranging from about 0% to about 10% of the vesicle-forming lipid.

29. The composition of claim 24, wherein the bacterial hemolysin is listeriolysin O.

30. The composition of claim 20, wherein the bacterial hemolysin is listeriolysin O.

31. The composition of claim 29, wherein the liposome contains between about five and about one-hundred molecules of the bacterial hemolysin per liposome.

32. The composition of claims 24 or 25, further comprising a pharmaceutically acceptable carrier.

33. A composition comprising a liposome consisting essentially of a plurality of vesicle-forming lipids, a bacterial hemolysin contained within the lumen of said liposome, a therapeutic agent or a diagnostic agent contained within the lumen of said liposome and a lysosomal fusion-inhibitor selected from the group consisting of a sulfatide and a lectin.

34. The composition of claim 33, wherein the liposome is a pH-sensitive liposome.

35. The composition of claim 33, wherein the bacterial hemolysin is listeriolysin O.

36. The composition of claim 34, wherein the bacterial hemolysin is listeriolysin O.

37. The composition of claim 35, wherein the liposome contains between about five and about one-hundred molecules of the bacterial hemolysin per liposome.

38. The composition of claims 33 or 34, further comprising a pharmaceutically acceptable carrier.

* * * * *